(12) United States Patent
Brehm et al.

(10) Patent No.: US 7,256,293 B2
(45) Date of Patent: Aug. 14, 2007

(54) IMIDAZOPYRIDINE INTERMEDIATES

(75) Inventors: Christof Brehm, Constance (DE); Wilm Buhr, Constance (DE)

(73) Assignee: Altana Pharma AG, Constance (DE)

( * ) Notice: Subject to any disclaimer, the term of this patent is extended or adjusted under 35 U.S.C. 154(b) by 130 days.

(21) Appl. No.: 10/555,057

(22) PCT Filed: May 4, 2004

(86) PCT No.: PCT/EP2004/050693

§ 371 (c)(1),
(2), (4) Date: Oct. 28, 2005

(87) PCT Pub. No.: WO2004/099203

PCT Pub. Date: Nov. 18, 2004

(65) Prior Publication Data

US 2006/0276499 A1   Dec. 7, 2006

(30) Foreign Application Priority Data

May 6, 2003   (EP) .................. 03010218

(51) Int. Cl.
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. .................. 546/121; 544/127; 544/333

(58) Field of Classification Search ................ 546/121; 544/127, 333
See application file for complete search history.

(56) References Cited

FOREIGN PATENT DOCUMENTS

| WO | 98/54188 A1 | 12/1998 |
|---|---|---|
| WO | 01/72754 A1 | 10/2001 |
| WO | 01/72755 A1 | 10/2001 |
| WO | 01/72756 A1 | 10/2001 |
| WO | 01/72757 A1 | 10/2001 |
| WO | 02/34749 A1 | 5/2002 |
| WO | 03/014120 A1 | 2/2003 |
| WO | 03/014123 A1 | 2/2003 |
| WO | 03/016310 A1 | 2/2003 |

OTHER PUBLICATIONS

Abe et al., J. med. Chem., "A novel class of orally active non-peptide bradykinin B2 receptor antagonists. 1. Construction of the basic framework", 1998, vol. 41, pp. 564-578.*

"Information Update: vol. 1-25, No. 6", *Drugs of the Future 2001*, vol. 26, No. 6, pp. 577-625, (2001).

* cited by examiner

*Primary Examiner*—Margaret D. Seaman
*Assistant Examiner*—Niloofar Rahmani
(74) *Attorney, Agent, or Firm*—The Nath Law Group; Joshua B. Goldberg; Sheldon M. McGee

(57) ABSTRACT

The invention relates to compounds of the formula 1,

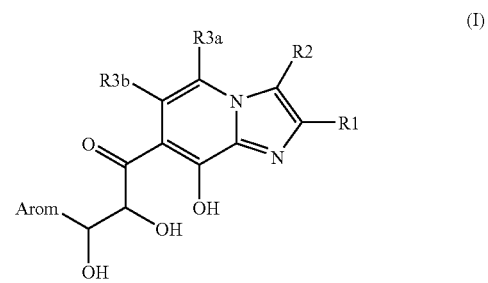

in which the substituents and symbols have the meanings indicated in the description. The compounds are valuable intermediates for the preparation of pharmaceutical active compounds.

10 Claims, No Drawings

IMIDAZOPYRIDINE INTERMEDIATES

TECHNICAL FIELD

The invention relates to novel compounds which are used in the pharmaceutical industry as valuable intermediates for the preparation of active compounds.

PRIOR ART

The international patent applications WO 98/54188, WO 01/72756, WO 01/72754, WO 01/72755, WO 01/72757, WO 02/34749, WO 03/016310, WO 03/014120 and WO 03/014123 disclose tricyclic imidazopyridine derivatives having a very specific substitution pattern, which should be suitable for the treatment of gastric and intestinal disorders, and certain processes for their preparation. In the document Drugs Fut 2001, 26 (6), 590, the preparation of tetrahydrobenzopyranes by cyclizaton using ortho-esters is disclosed.

DESCRIPTION OF THE INVENTION

The invention relates to a new process for the production of the tricyclic imidazopyridine derivatives mentioned above, and to valuable intermediates used in said processes.

The invention thus relates in a first aspect to compounds of the formula 1

(1)

R1 is hydrogen, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl or hydroxy-1-4C-alkyl, R2 is hydrogen, 1-4C-alkyl, aryl, 3-7C-cycloalkyl, 3-7C-cycloalkyl-1-4C-alkyl, 1-4C-alkoxycarbonyl, hydroxy-1-4C-alkyl, halogen, 2-4C-alkenyl, 2-4C-alkynyl, fluoro-1-4C-alkyl, cyanomethyl R3a is hydrogen, halogen, fluoro-1-4C-alkyl, 1-4C-alkyl, 2-4C-alkenyl, 2-4C-alkynyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the radical —CO—NR31R32, R3b is hydrogen, halogen, fluoro-1-4C-alkyl, 1-4C-alkyl, 2-4C-alkenyl, 2-4C-alkynyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the radical —CO—NR31R32,
where
R31 is hydrogen, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl, or where
R31 and R32 together, including the nitrogen atom to which both are bonded, are a pyrrolidino, piperidino, piperazino, N-1-4C-alkylpiperazino or morpholino radical, Arom is a mono- or bicyclic aromatic radical substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuyl), thiophenyl (thienyl), benzothiophenyl (benzothienyl), thiazolyl, isoxazolyl, pyridinyl, pyrimidinyl, quinolinyl and isoquinolinyl,
where
R4 is hydrogen, 1-4C-alkyl, hydroxy-1-4C-alkyl, 1-4C-alkoxy, 2-4C-alkenyloxy, 1-4C-alkylcarbonyl, carbonyl, 1-4C-alkoxycarbonyl, carboxy-1-4C-alkyl, 1-4C-alkoxycarbonyl-1-4C-alkyl, halogen, hydroxyl, aryl, aryl-1-4C-alkyl, aryloxy, aryl-1-4C-alkoxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl,
R5 is hydrogen, 1-4C-alkyl, 1-4C-alkoxy, 1-4C-alkoxycarbonyl, halogen, trifluoromethyl or hydroxyl,
R6 is hydrogen, 1-4C-alkyl or halogen and
R7 is hydrogen, 1-4C-alkyl or halogen,
where
aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy, hydroxyl and cyano, and their salts.

1-4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and the methyl radical.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkyl-1-4C-alkyl represents one of the aforementioned 1-4C-alkyl radicals, which is substituted by one of the aforementioned 3-7C-cycloalkyl radicals. Examples which may be mentioned are the cyclopropylmethyl, the cyclohexylethyl radical.

1-4C-Alkoxy represents radicals, which in addition to the oxygen atom contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radical.

1-4C-Alkloxy-1-4C-alkyl represents one of the aforementioned 1-4C-alkyl radicals, which is substituted by one of the aforementioned 1-4C-alkoxy radicals. Examples which may be mentioned are the methoxymethyl, the methoxyethyl radical and the butoxyethyl radical.

1-4C-Alkoxycarbonyl represents a carbonyl group, to which one of the aforementioned 1-4C-alkoxy radicals is bonded. Examples which may be mentioned are the methoxycarbonyl ($CH_3O$—C(O)—) and the ethoxycarbonyl radical ($CH_3CH_2O$—C(O)—).

2-4C-Alkenyl represents straight-chain or branched alkenyl radicals having 2 to 4 carbon atoms. Examples which may be mentioned are the 2-butenyl, 3-butenyl, 1-propenyl and the 2-propenyl radical (allyl radical).

2-4C-Alkynyl represents straight-chain or branched alkynyl radicals having 2 to 4 carbon atoms. Examples which may be mentioned are the 2-butynyl, 3-butynyl, and preferably the 2-propynyl, radical (propargyl radical).

Fluoro-1-4C-alkyl represents one of the aforementioned 1-4C-alkyl radicals, which is substituted by one or more fluorine atoms. An example which may be mentioned is the trifluoromethyl radical.

Hydroxy-1-4C-alkyl represents aforementioned 1-4C-alkyl radicals, which are substituted by a hydroxy group. Examples which may be mentioned are the hydroxymethyl, the 2-hydroxyethyl and the 3-hydroxypropyl radical.

Halogen within the meaning of the invention is bromo, chloro and fluoro.

1-4C-Alkoxy-1-4C-alkoxy represents one of the aforementioned 1-4C-alkoxy radicals, which is substituted by a further 1-4C-alkoxy radical. Examples which may be mentioned are the radicals 2-(methoxy)ethoxy ($CH_3$—O—$CH_2$—$CH_2$—O—) and 2-(ethoxy)ethoxy ($CH_3$—$CH_2$—O—$CH_2$—$CH_2$—O—).

1-4C-Alkoxy-1-4C-alkoxy-1-4C-alkyl represents one of the aforementioned 1-4C-alkoxyl1-4Calkyl radicals, which is substituted by one of the aforementioned 1-4C-alkoxy radicals. An example which may be mentioned is the radical 2-(methoxy)ethoxy-methyl ($CH_3$—O—$CH_2$—$CH_2$O—$CH_2$—).

Fluoro-1-4C-alkoxy-1-4C-alkyl represents one of the aforementioned 1-4C-alkyl radicals, which is substituted by a fluoro-1-4C-alkoxy radical. Fluoro-1-4C-alkoxy in this case represents one of the aforementioned 1-4C-alkoxy radicals, which is wholly or mainly substituted by fluorine. Examples of wholly or mainly fluoro-substituted 1-4C-alkoxy which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radical.

1-7C-Alkyl denotes straight-chain or branched alkyl radicals having 1 to 7 carbon atoms. Examples which may be mentioned are the heptyl, isoheptyl-(5-methylhexyl), hexyl, isohexyl-(4-methylpentyl), neohexyl-(3,3-dimethylbutyl), pentyl, isopentyl-(3-methylbutyl), neopentyl-(2,2-dimethylpropyl), butyl, isobutyl, sec-butyl, tert-butyl, propyl, isopropyl, ethyl and methyl radicals.

2-4C-Alkenyloxy represents a radical, which in addition to the oxygen atom contains a 2-4C-alkenyl radical. An example which may be mentioned is the allyloxy radical.

1-4C-Alkylcarbonyl represents a radical, which in addition to the carboyl group contains one of the aforementioned 1-4C-alkyl radicals. An example which may be mentioned is the acetyl radical.

Carboxy-1-4C-alkyl for example represents the carboxymethyl (—$CH_2COOH$) or the carboxyethyl radical (—$CH_2CH_2COOH$).

1-4C-Alkoxycarbonyl-1-4C-alkyl represents one of the aforementioned 1-4C-alkyl radicals, which is substituted by one of the aforementioned 1-4C-alkoxycarbonyl radicals. An example which may be mentioned is the ethoxycarbonylmethyl radical ($CH_3CH_2OC(O)CH_2$—).

Aryl-1-4C-alkyl represents an aryl-substituted 1-4C-alkyl radical. An example which may be metnioned is the benzyl radical.

Aryl-1-4C-alkoxy represents an aryl-substituted 1-4C-alkoxy radical. An example which may be mentioned is the benzyloxy radical.

Mono- or di-1-4C-alkylamino radicals contain, in addition to the nitrogen atom, one or two of the aforementioned 1-4C-alkyl radicals. Di-1-4C-alkylamino is preferred and here, in particular, dimethyl-, diethyl- or dilsopropylamino.

1-4C-Alkylcarbonylamino represents an amino group to which a 1-4C-alkylcarbonyl radical is bonded. Examples which may be mentioned are the propionylamino ($C_3H_2C(O)NH$—) and the acetylamino radical (acetamido radical) ($CH_3C(O)NH$—).

1-4C-Alkoxycarbonylamino represents an amino radical, which is substituted by one of the aforementioned 1-4C-alkoxycarbonyl radicals. Examples which may be mentioned are the ethoxycarbonylamino and the methoxycarbonylamino radical.

1-4C-Alkoxy-1-4C-alkoxycarbonyl represents a carbonyl group, to which one of the aforementioned 1-4C-alkoxy-1-4C-alkoxy radicals is bonded. Examples which may be mentioned are the 2-(methoxy)ethoxycarbonyl ($CH_3$—O—$CH_2CH_2$—O—CO—) and the 2-(ethoxy)ethoxy-carbonyl radical ($CH_3CH_2$—O—$CH_2CH_2$—O—CO—).

1-4C-Alkoxy-1-4C-alkoxycarbonylamino represents an amino radical, which is substituted by one of the aforementioned 1-4C-alkoxy-1-4C-alkoxycarbonyl radicals. Examples which may be mentioned are the 2-(methoxy)ethoxycarbonylamino and the 2-(ethoxy)ethoxycarbonyl-amino radical.

Arom radicals which may be mentioned are, for example, the following substituents: 4-acetoxyphenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3-methoxyphenyl, 3,5-bis(trifluoromethyl)phenyl, 4-butoxyphenyl, 2-chlorophenyl, 3-chlorophenyl, 4-chlorophenyl, 2-chloro-6-fluorophenyl, 3-chloro-4-fluorophenyl, 2-chloro-5-nitrophenyl, 4-chloro-3-nitrophenyl, 3-(4-chlorophenoxy)phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy-4-hydroxyphenyl, 2-fluorophenyl, 4-fluorophenyl, 4-hydroxyphenyl, 2-hydroxy-5-nitrophenyl, 3-methoxy-2-nitrophenyl, 3-nitrophenyl, 2,3,5-trichlorphenyl, 2,4,6-trihydroxyphenyl, 2,3,4-trimethoxyphenyl, 2-hydroxy-1-naphthyl, 2-methoxy-1-naphthyl, 4-methoxy-1-naphthyl, 1-methyl-2-pyrrolyl, 2-pyrrolyl, 3-methyl-2-pyrroly, 3,4-dimethyl-2-pyrrolyl, 4-(2-methoxycarbonylethyl)-3-methyl-2-pyrrolyl, 5-ethoxycarbonyl-2,4-dimethyl-3-pyrrolyl, 3,4-dibromo-5-methyl-2-pyrrolyl, 2,5-dimethyl-1-phenyl-3-pyrrolyl, 5-carboxy-3-ethyl-4-methyl-2-pyrrolyl, 3,5-dimethyl-2-pyrrolyl, 2,5-dimethyl-1-(4-trifluormethylphenyl)-3-pyrrolyl, 1-(2,6-dichloro-4-trifluoromethylphenyl)-2-pyrrolyl, 1-(2-nitrobenzyl)-2-pyrrolyl, 1-(2-fluorophenyl)-2-pyrrolyl, 1-(4-trifluoromethoxyphenyl)-2-pyrrodyl, 1-(2-nitrobenzyl)-2-pyrrolyl, 1-(4-ethoxycarbonyl)-2,5-dimethyl-3-pyrrolyl, 5-chloro-1,3-dimethyl-4-pyrazolyl, 5-chloro-1-methyl-3-trifluoromethyl-4-pyrazolyl, 1-(4-chlorobenzyl)-5-pyrazolyl, 1,3-dimethyl-5-(4-chlorphenoxy)-4-pyrazolyl, 1-methyl-3-trifluomethyl-5-(3-trifluoromethylphenoxy)-4-pyrazolyl, 4-methoxycarbonyl-1-(2,6-dichlorophenyl)-5-pyrazolyl, 5-allyloxy-1-methyl-3-trifluoromethyl-4-pyrazolyl, 5-chloro-1-phenyl-3-trifluoromethyl-4-pyrazolyl, 3,5-dimethyl-1-phenyl-4-imidazolyl, 4-bromo-1-methyl-5-imidazolyl, 2-butylmidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-3-indolyl, 6-benzyloxy-3-indolyl, 2-methyl-5-nitro-3-indolyl, 4,5,6,7-tetrafluoro-3-indolyl, 1-(3,5-difluorobenzyl)-3-indolyl, 1-methyl-2-(4-trifluorophenoxy)-3-indolyl, 1-methyl-2-benzimidazolyl, 5-nitro-2-furyl, 5-hydroxymethyl-2-furyl, 2-furyl, 3-furyl, 5-(2-nitro-4-trifluoromethylphenyl)-2-furyl, 4-ethoxycarbonyl-5-methyl-2-furyl, 5-(2-trifluromethoxyphenyl)-2-furyl, 5-(4-methoxy-2-nitrophenyl)-2-furyl, 4-bromo-2-furyl, 5-dimethylamino-2-furyl, 5-bromo-2-furyl, 5-sulfo-2-furyl, 2-benzofuryl, 2-thienyl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2-thienyl, 3-phenoxy-2-thienyl, 5-carboxy-2-thienyl, 2,5-dichloro-3-thienyl, 3-methoxy-2-thienyl, 2-benzothianyl, 3-methyl-2-benzothienyl, 2-bromo-5-chloro-3-benzothienyl, 2-thiazolyl, 2-amino-4-chloro-5-thiazolyl, 2,4-dichloro-5-thiazolyl, 2-diethylamino-5-thiazolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6-dichloro-4-pyridyl, 3-chloro-5-trifluoromethyl-2-pyridyl, 4,6-dimethyl-2-pyridyl, 4-(4-chlorphenyl)-3-pyridyl, 2-chloro-5-methoxycarbonyl-6-methyl-4-phenyl-3-pyridyl, 2-chloro-3-pyridyl, 6-(3-trifluoromethylphenoxy)-3-pyridyl, 2-(4-chlorophenoxy)-3-pyridyl, 2,4-dimethoxy-5-pyrimidinyl, 2-quinolinyl, 3-quinolinyl, 4-quinolinyl, 2-chloro-3-quinolinyl, 2-chloro-6-methoxy-3-quinolinyl, 8-hydroxyl-2-quinolinyl and 4-isoquinolinyl.

Possible salts of compounds of the formula I—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluensulfonic acid, methanesulfonic acid or 3-hydroxy-2-naphthoic acid, where the acids are used in salt preparation—depending on whether a mono- or polybasic acid is concerned and on which salt is desired—in an equimolar quantitative ratio or one differing therefrom.

It is known to the person skilled in the art that the compounds according to invention and their salts, if, for example, they are isolated in crystalline form, can contain various amounts of solvents. The invention therefore also comprises all solvates and in particular all hydrates of the compounds of the formula I, and also all solvates and in particular all hydrates of the salts of the compounds of the formula I.

The compounds of the formula 1 have two chiral centers in the parent structure. The invention thus relates to all conceivable stereoisomers in any desired mixing ratio to one another, including the pure enanitomers, which are a preferred subject of the invention.

One embodiment (embodiment 1) of the invention are compounds of the formula 1, in which R1 is 1-4C-alkyl and R2, R3a, R3b and Arom have the meanings as described in the outset.

Another embodiment (embodiment 2) of the invention are compounds of the formula 1, in which R2 is 1-4C-alkyl and R1, R3a, R3b and Arom have the meanings as described in the outset.

Another embodiment (embodiment 3) of the invention are compounds of the formula 1, in which R3a is hydrogen and R1, R2, R3b and arom have the meanings as described in the outset.

Another embodiment (embodiment 4) of the invention are compounds of the formula 1, in which R3b is hydrogen and R1, R2, R3a and Arom have the meanings as described in the outset.

Another embodiment (embodiment 5) of the invention are compounds of the formula 1, in which Arom is phenyl and R1, R2, R3a and R3b have the meanings as described in the outset.

Compounds to be emphasized are those of the formula 1, in which

R1 is hydrogen, 1-4C-alkyl, 3-7C-cycloalkyl, 1-4C-alkoxy-1-4C-alkyl, 2-4C-alkynyl or fluoro-1-4C-alkyl, R2 is hydrogen, 1-4C-alkyl, aryl, hydroxy-1-4C-alkyl, halogen, 2-4C-alkenyl, 2-4C-alkynyl, fluoro-1-4C-alkyl R3a is hydrogen, R3b is hydrogen, halogen, 1-4C-alkyl or the radical-CO—31R32, where R31 is hydrogen, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino or morpholino radical, Arom is a monocyclic aromatic radical substituted by R4, R5, R6 and R7, which is selected from the group consisting of phenyl, furanyl (furyl) and thiophenyl (thienyl), where R4 is hydrogen, 1-4C-alkyl, hydroxy-1-4C-alkyl, 1-4C-alkoxy, 1-4C-alkylcarbonyl, carboxyl, 1-4C-alkoxycarbonyl, halogen, hydroxyl, trifluoromethyl, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen, trifluoromethyl or hydroxyl, R6 is hydrogen and R7 is hydrogen, and their salts.

Compounds to be particularly emphasized are those of the formula 1, in which

R1 is 1-4C-alkyl or 1-4C-alkoxy-1-4C-alkyl,

R2 is hydrogen, 1-4C-alkyl, phenyl, hydroxy-1-4C-alkyl or halogen

R3a is hydrogen,

R3b is hydrogen,

Arom is phenyl, furanyl (furyl) or thiophenyl (thienyl), and their salts.

Among the compounds according to the invention, including the embodiments 1 to 5 and the compounds to be emphasized and to be particularly emphasized, the optically pure compounds of the formula 1*

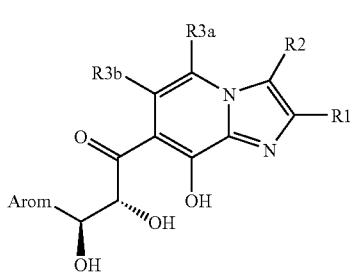 (1*)

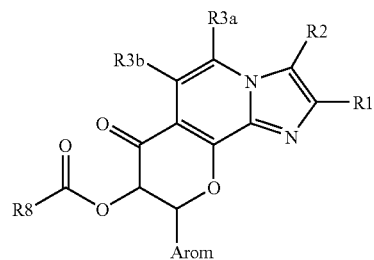 (2)

are preferred.

Preferred compounds of the formula 1* are those in which
R1 is hydrogen, 1-4C-alkyl, 3-7C-cycloalkyl, 1-4C-alkoxy-1-4C-alkyl, 2-4C-alkynyl or fluoro-1-4C-alkyl,
R2 is hydrogen, 1-4C-alkyl, aryl, hydroxy-1-4C-alkyl, halogen, 2-4C-alkenyl, 2-4C-alkynyl, fluoro-1-4C-alkyl
R3a is hydrogen,
R3b is hydrogen, halogen, 1-4C-alkyl or the radical —CO—NR31R32.
where
R31 is hydrogen, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidine, piperidino or morpholino radical
Arom is phenyl, furanyl (furyl) or thiophenyl (thienyl), and their salts.

Compounds with exemplary substituents to be particularly emphasized are those of the formula 1*, in which
R1 is hydrogen, methyl, cyclopropyl, methoxymethyl or trifluoromethyl,
R2 is hydrogen, methyl, phenyl, hydroxymethyl, fluoro, chloro, bromo, ethynyl, trifluomethyl
R3a is hydrogen,
R3b is hydrogen, fluorine, methyl or the radical —CO—N(CH₃)₂,
Arom is a phenyl radical and their salts.

Particularly preferred exemplary compounds of the formula 1* are those, in which
R1 is methyl,
R2 is hydrogen, methyl, fluoro, chloro, bromo, hydroxymethyl or trifluoromethyl
R3a is hydrogen,
R3b is hydrogen,
Arom is a phenyl radical and their salts.

Particularly preferred are the compounds given as final products in the examples, and their salts.

The invention further relates to the use of compounds of the formula 1, in which R1, R2, R3a, R3b and Arom have the meanings indicated in the outset, for the preparation of compounds of the formula 2 in which R1, R2, R3, R3b and Arom have the meanings indicated in the outset, and R8 is hydrogen, 1-4C-Alkyl or aryl, as indicated in the outset, and their salts.

The preparation of the compounds of the formula 2 is effected, as shown for example in scheme 1, such that the compounds of the formula 1, in which R1, R2, R3a, R3b and Arom have the meanings indicated in the outset, are reacted with ortho-esters R8-C(OR9)₃, in which R8 is hydrogen, 1-4C-Alkyl or aryl, as indicated in the outset, and R9 is 1-4C-alkyl.

Scheme 1:

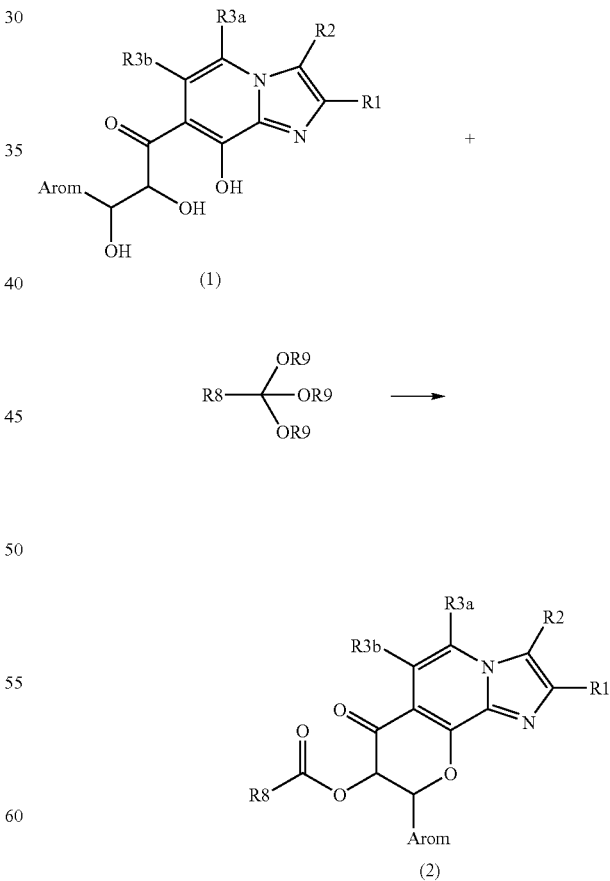

To be emphasized according to the invention is the use of compounds of the formula 1* for the preparation of compounds of the formula 2*,

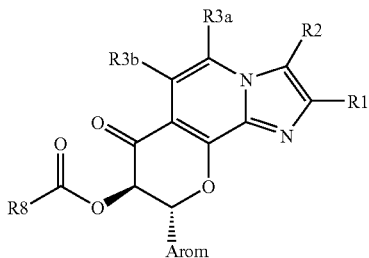

(2*)

in which R1, R2, R3a, R3b and Arom have the meanings indicated in the outset and R8 has the meaning hydrogen, 1-4C-Alkyl or aryl, as indicated in the outset, and their salts.

The conversion of a compound of the formula 1 into a cyclization product of the formula 2 according to scheme 1 is carried out in a manner known to the expert, e.g. similar to that disclosed in Drugs Fut 2001, 26 (6), 590.

The compounds of the formula 1 according to the invention, in which R1, R2, R3a, R3b and Arom have the meanings indicated in the outset, can be prepared from the compounds of the formula 3, in which R1, R2, R3a, R3b and Arom have the meanings indicated in the outset,

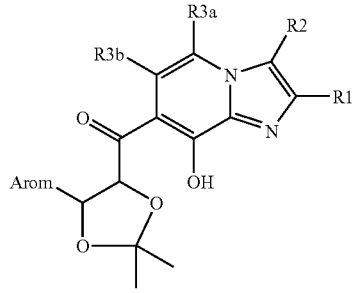

(3)

as shown by way of example in scheme 2 below for the compounds 1* and 3*, by reaction with a mineral acid:

Scheme 2:

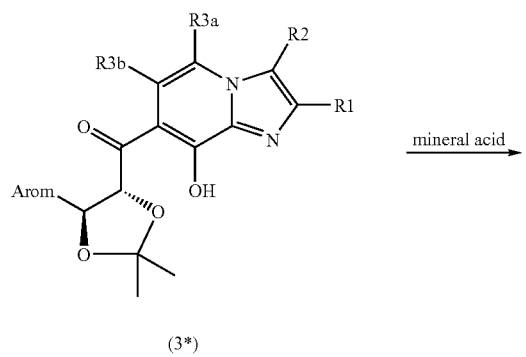

(3*)

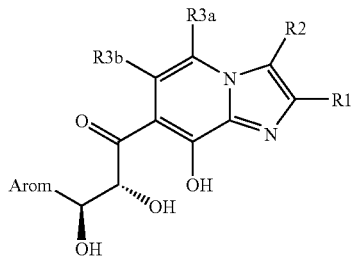

(1*)

Preferred mineral acids for the reaction shown in scheme 2 are phosphoric acid, hydrochloric acid or sulphuric acid.

Starting compounds of the formula 3 are known (see WO01/72755 or WO 02/34749) or they can be prepared in a known manner in analogy to known compounds as shown by way of example for the compound 3* in scheme 3 below.

Scheme 3:

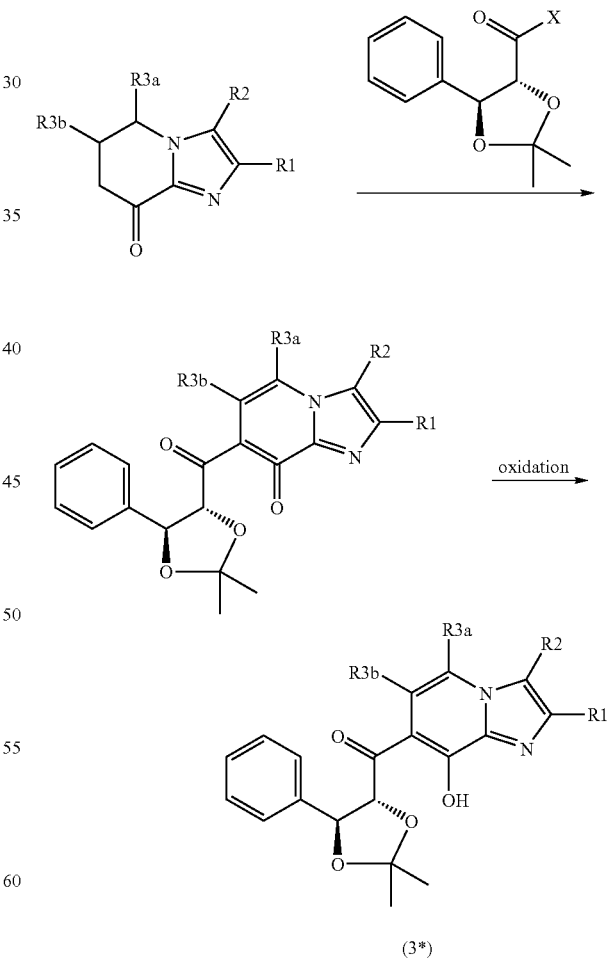

(3*)

The group X in scheme 3 is a suitable leaving group, for example a halogen atom, preferably chlorine, or a 1-4C alkoxy group, preferably methoxy.

The following examples serve to explain the invention in greater detail without restricting it. Likewise, further compounds of the formula 1, whose preparation is not described explicity, can be prepared in an analogous manner or in a manner familiar per set to the person skilled in the art using customary process techniques. The abbreviation min stands for minute(s), h for hour(s) and m. p. for melting point.

EXAMPLES

Compounds of the Formula 1

1. 2-Methyl-7-[(2R,3S)-2,3-diyhdroxy-3-phenylpropan-1-on-1-yl]imidazo[1,2-a]-pyridin-8-ol 156 g (0.442 mol) of 2-Methyl-7-[(2R,3S)-2,3-O,O-isopropylidan-2,3-dioxy-3-phenylpropan-1-on-1-yl]-imidazo[1,2-a]-pyridin-8-ol are dissolved in 3 l of 6 molar hydrochloric acid during 30 min. After stirring for 1 h at room temperature, the reaction mixture is cooled with an ice bath and neutralized to pH 6.5 to 7 using a 6 molar sodium hydroxide solution. The precipitate is filtered off, washed with water and for the most part redissolved in 0.5 molar hydrochloric acid. The remaining residue is separated by filtration and the filtrate is neutralized again to pH 6.5 to 7 using a 6 molar sodium hydroxide solution. The resulting precipitate is filtered off and dried in vacuum to afford 84.6 g (0.271 mol, yield 61%) of the title compound in analytical pure quality as a beige-brown solid.

m. p.: 110-115° C. (water)

2. 2,3-Dimethyl-7-[(2R,3S)-2,3-diyhdroxy-3-phenyl-propan-1-on-1-yl]imidazo[1,2-a]-pyridin-8-ol 10 g (0.027 mol) of 2,3-Dimethyl-7-[(2R,3S)-2,3-O,O-isopropyliden-2,3-dioxy-3-phenylpropan-1-on-1-yl]-imidazo[1,2,-a]-pyridin-8-ol are dissolved in 0 ml of 6 molar hydrochloric acid. After stirring for 30 min at room temperature, the reaction mixture is cooled with an ice bath and neutralized to pH 6.5 using a 6 molar sodium hydroxide solution. The resulting residue is filtered off, washed with water and dried in vacuum at 55° C. The crude product is purified by chromatography on silica gel (eluent dichloromethane/methanol: 5/1) to give 5.77 g (0.018 mol, yield 65%) of the title compound as ochre crystals.

$^1$H-NMR (CDCl$_3$): (ppm)=2.25 (3H, s), 2.38 (3H, s), 5.32 (1H, d), 5.55 (1H, d), 7.13 (1H, d), 7.18-7.25 (3H, m), 7.51 (2H, dd), 7.70 (1H, d).

Use of Compounds of the Formula 1 According to the Invention for the Preparation of Compounds of the Formula 2

A. (8R,9R)-8-Acetoxy-2-methyl-9-phenyl-7H-8,9-dihydro-pyrano[2,3-c]imidazo[1,2-a]-pyridin-7-on 150 ml (1.166 mol) of orthoacetic acid trimethyl ester, 7.5 g (0.030 mol) of pyridrium-p-toluenesulfonate and 13.5 ml (0.358 mol) of formic acid are added at room temperature to a solution of 93.4 g (0.299 mol) of 2-Methyl-7-[(2R,3S)-2,3-diyhdroxy-3-phenylpropan-1-on-1-yl]imidazo-[1,2-a]-pyridin-8-ol in 2.3 l of dichloromethane. After 2 h stirring at room temperature the reaction mixture is poured onto 1.5 l of a 0.25 molar sodium bicarbonate solution. After 15 min stirring at room temperature the organic phase is separated and the sequence phase extracted with methylene chloride. The combined organic layers are washed with saturated sodium bicarbonate solution, dried over sodium sulphate and the solvent removed under vacuum. The resulting solid is recrystalized from diisopropyl ether and dried in vacuum to afford 91.3 g (0.271 mol, yield 90.8%) of the title compound in form of lightly yellow crystals.

m. p.: 220-222° C. (diisopropyl ether)

B. (8R,9R)-8-Acetoxy-2,3-dimethyl-9-phenyl-7H-8,9-dihydro-pyrano[2,3-c]imidazo[1,2-a]-pyridin-7-on 3.18 ml (0.025 mol) of orthoacetic acid trimethyl ester, 0.16 g (0.0008 mol) of pyridinium-p-toluenesulfonate and 0.28 ml (0.007 mol) of formic acid are added at room temperature to a solution of 2 g (0.006 mol) of 2,3-dimethyl-7-[(2R,3S)-2,3-dihydroxy-3-phenylpropan-1-on-1-yl]imidazo-[1,2-a]-pyridin-8-ol in 40 ml of dichloromethane. After stirring for 16 h at room temperature, the reaction mixture is diluted with dichloromethane, washed with saturated sodium bicarbonate solution, dried over sodium sulphate and the solvent removed under vacuum. The crude product is purified by filtration over a thin layer of silica gel (solvent dichloromethane/methanol: 100/1). After removal of the solvent, 1.8 g (0.005 mol, yield 84%) of the title compound is obtained in form of colourless crystals.

m. p.: 205-206° C. (diethyl ether/acetone).

C. (8R,9R)-2,3-Dimethyl-8-isobutyryloxy-9-phenyl-7H-8,9-dihydro-pyrano[2,3-c]imidazo-[1,2-a]pyridin-7-on 1.81 g (0.012 mol) of ortholsobutyric acid trimethyl ester, 0.08 g (0.0003 mol) of pyridinium-p-toluenesulfonate and 0.14 ml (0.004 mol) of formic acid are added at room temperature to a solution of 1 g (0.003 mol) of 2,3-dimethyl-7-[(2R,3S)-2,3-dihydroxy-3-phenylpropan-1-on-1-yl]imidazo-[1,2-a]-pyridin-8-ol in 10 ml of dichloromethane. After stirring for 16 h at room temperature, the reaction mixture is poured onto a saturated sodium bicarbonate solution, the aqueous layer extracted with dichloromethane, the combined organic layers dried over sodium sulphate and the solvent removed under vacuum. The crude product is purified by chromatography on silica gel (eluent dichloromethane/methanol: 100/3) to give 0.98 g (0.003 mol, yield 85%) of the title compound in form of colourless crystals.

m. p.: 207-208° C. (acetone).

Commercial Utility

The compounds of the formula 1 and their salts are valuable intermediates for the preparation of active compounds, such as are disclosed, for example, in the international patent applications WO 98/54188, WO 01/72756, WO 01/72754, WO 01/72757, WO 02/34749, WO 03/016310, WO 03/014120 and WO 03/014123.

The invention claimed is:
1. A compound of the formula 1

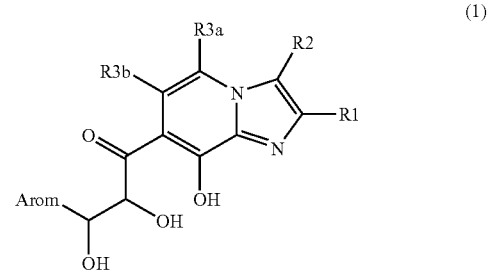

(1)

in which

R1 is hydrogen, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl or hydroxy-1-4C-alkyl, R2 is hydrogen, 1-4C-alkyl, aryl, 3-7C-cycloalkyl-1-4C-alkyl, 1-4C-alkoxycarbonyl, hydroxy-1-4C-alkyl, halogen, 2-4C-alkenyl, 2-4C-alkynyl, fluoro-1-4C-alkyl, cyanomethyl, R3a is hydrogen, halogen, fluoro-1-4C-alkyl, 1-4C-alkyl, 2-4C-alkenyl, 2-4C-alkynyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the radical —CO—NR31R32, R3b is hydrogen, halogen, fluoro-1-4C-alkyl, 1-4C-alkyl, 2-4C-alkenyl, 2-4C-alkynyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the radical —CO—NR31R32, where R31 is hydrogen, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino radical, Arom is a mono- or bicyclic aromatic radical substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R4 is hydrogen, 1-4C-alkyl, hydroxy-1-4C-alkyl, 1-4C-alkoxy, 2-4C-alkenyloxy, 1-4C-alkylcarbonyl, carboxyl, 1-4C-alkoxycarbonyl, carboxy-1-4C-alkyl, 1-4C-alkoxycarbonyl-1-4C-alkyl, halogen, hydroxyl, aryl, aryl-1-4C-alkyl, aryloxy, aryl-1-4C-alkoxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen, trifluoromethyl or hydroxyl, R6 is hydrogen, 1-4C-alkyl or halogen and R7 is hydrogen, 1-4C-alkyl or halogen, where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy, hydroxyl and cyano, or a salt, thereof.

2. A compound of the formula 1 according to claim 1, in which

R1 is hydrogen, 1-4C-alkyl, 3-7C-cycloalkyl, 1-4C-alkoxy-1-4C-alkyl, 2-4C-alkynyl or fluoro-1-4C-alkyl, R2 is hydrogen, 1-4C-alkyl, aryl, hydroxy-1-4C-alkyl, halogen, 2-4C-alkenyl, 2-4C-alkynyl, fluoro-1-4C-alkyl, R3a is hydrogen, R3b is hydrogen, halogen, 1-4C-alkyl or the radical —CO—NR31R32, where R31 is hydrogen, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino radical, Arom is a monocyclic aromatic radical substituted by R4, R5, R6 and R7, which is selected from the group consisting of phenyl, furanyl (furyl) and thiophenyl (thienyl), where R4 is hydrogen, 1-4C-alkyl, hydroxy-1-4C-alkyl, 1-4C-alkoxy, 1-4C-alkylcarbonyl, carboxyl, 1-4C-alkoxycarbonyl, halogen, hydroxyl, trifluoromethyl, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen, trifluoromethyl or hydroxyl, R6 is hydrogen and R7 is hydrogen, or a salt, thereof.

3. A compound of the formula 1 according to claim 1, in which

R1 is 1-4C-alkyl or 1-4C-alkoxy-1-4C-alkyl,

R2 is hydrogen, 1-4C-alkyl, phenyl, hydroxy-1-4C-alkyl, halogen,

R3a is hydrogen,

R3b is hydrogen,

Arom is phenyl, furanyl (furyl) or thiophenyl (thienyl), or a salt, thereof.

4. A compound according to claim 1, characterized by the general formula 1*, (1*)

[Structural formula showing imidazopyridine core with R3a, R3b, R2, R1 substituents and Arom-C(O)-CH(OH)-CH(OH)- side chain]

in which

R1 is hydrogen, 1-4C-alkyl, 3-7C-cycloalkyl, 1-4C-alkoxy-1-4C-alkyl, 2-4C-alkynyl or fluoro-1-4C-alkyl, R2 is hydrogen, 1-4C-alkyl, aryl, hydroxy-1-4C-alkyl, halogen, 2-4C-alkenyl, 2-4C-alkynyl, fluoro-1-4C-alkyl, R3a is hydrogen, R3b is hydrogen, halogen, 1-4C-alkyl or the radical —CO—NR31R32, where
R31 is hydrogen, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidino, piperidino or morpholino radical,
Arom is phenyl, furanyl (furyl) or thiophenyl (thienyl),
or salt, thereof.

5. A compound according to claim 1, characterized by formula 1*

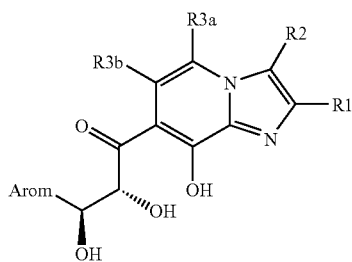

(1*)

in which
R1 is hydrogen, methyl, cyclopropyl, methoxymethyl or trifluoromethyl,
R2 is hydrogen, methyl, phenyl, hydroxymethyl, chloro, bromo, ethynyl, trifluoromethyl,
R3a is hydrogen,
R3b is hydrogen, fluorine, methyl or the radical —CO—N(CH$_3$)$_2$,
Arom is a phenyl radical,
or a salt, thereof.

6. A compound according to claim 1, characterized by formula 1*

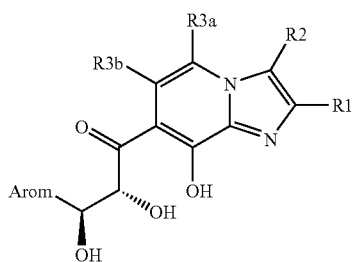

(1*)

in which
R1 is methyl,
R2 is hydrogen, methyl, fluoro, chloro, bromo, hydroxymethyl or trifluoromethyl,
R3a is hydrogen,
R3b is hydrogen,
Arom is a phenyl radical,
or a salt, thereof.

7. A process of preparing a compound of the formula 2 or a salt, thereof,

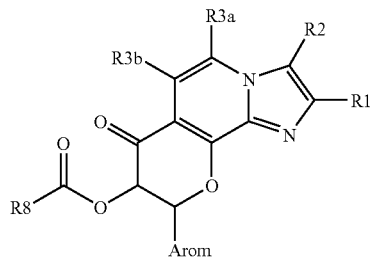

(2)

in which R1, R2, R3a, R3b and Arom have the meanings indicated in claim 1, and R8 is hydrogen, 1-4C-Alkyl or aryl, where aryl has the meaning as indicated in claim 1, comprising reacting a compound of the formula 1

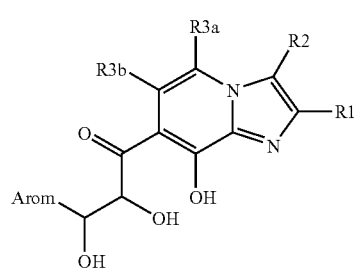

(1)

or a hydrate, solvate, salt, hydrate of a salt or solvate of a salt thereof,
in which R1, R2, R3a, R3b and Arom have the meanings indicated in claim 1,
with an ortho-ester of the formula R8-C(OR9)$_3$, in which R8 is hydrogen, 1-4C-Alkyl or aryl,
wherein aryl has the meanings indicated in claim 1, and R9 is 1-4C-alkyl.

8. A process of preparing a compound of the formula 2* or a salt, thereof,

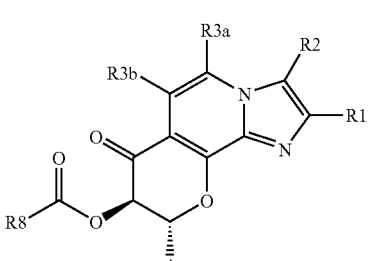

(2*)

in which R1, R2, R3a, R3b and Arom have the meanings indicated in claim 4, and R8 is hydrogen, 1-4C-Alkyl or aryl, where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy, hydroxyl and cyano, comprising reacting a compound of the formula 1*

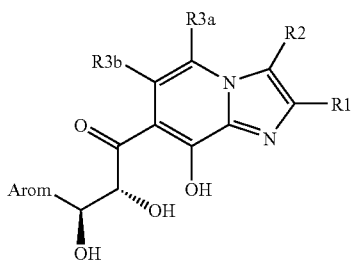
(1*)

or a hydrate, solvate, salt, hydrate of a salt or solvate of a salt thereof, in which R1, R2, R3a, R3b and Arom have the meanings indicated in claim 4, with an ortho-ester of the formula R8-C(OR9)$_3$, in which R8 is hydrogen, 1-4C-Alkyl or aryl, wherein aryl has the meanings indicated above, and R9 is 1-4C-alkyl.

9. A process for the preparation of a compound of the formula 1 as claimed in claim 1, in which R1, R2, R3a, R3b and Arom have the meanings indicated in claim 1, which comprises deprotection of a compound of the formula 3,

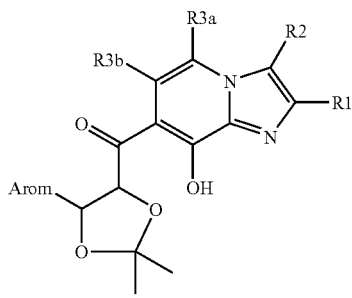
(3)

in which R1, R2, R3a, R3b and Arom have the meanings indicated in claim 1, by reacting said compound with a mineral acid.

10. A process for the preparation of a compound of the formula 1* as claimed in claim 4, in which R1, R2, R3a, R3b and Arom have the meanings indicated in claim 4, which comprises deprotection of a compound of the formula 3*,

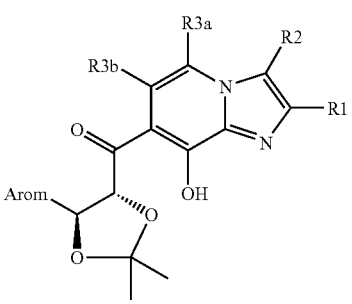
(3*)

in which R1, R2, R3a, R3b and Arom have the meanings indicated in claim 4, by reacting said compound with a mineral acid.

* * * * *